(12) United States Patent
Svoboda (10) Patent No.: US 9,956,060 B2
(45) Date of Patent: May 1, 2018

(54) DENTAL PROSTHESES CEMENTED ONTO IMPLANTS AND/OR ABUTMENTS HAVING A REVERSE MARGIN

(71) Applicant: Dr. Emil Svoboda Dentistry Professional Corporation, Brampton (CA)

(72) Inventor: Emil Svoboda, Brampton (CA)

(73) Assignee: CSD Connection Systems for Dentistry Inc., Brampton, Ontario (CA)

(\*) Notice: Subject to any disclaimer, the term of this patent is extended or adjusted under 35 U.S.C. 154(b) by 125 days.

(21) Appl. No.: 14/327,594

(22) Filed: Jul. 10, 2014

(65) Prior Publication Data

US 2016/0008105 A1    Jan. 14, 2016

(51) Int. Cl.
| | | |
|---|---|---|
| *A61C 8/00* | (2006.01) | |
| *A61C 5/70* | (2017.01) | |
| *A61C 13/083* | (2006.01) | |

(52) U.S. Cl.
CPC .............. *A61C 8/0069* (2013.01); *A61C 5/70* (2017.02); *A61C 8/005* (2013.01); *A61C 8/0022* (2013.01); *A61C 8/0048* (2013.01); *A61C 8/0068* (2013.01); *A61C 8/0075* (2013.01); *A61C 8/0077* (2013.01); *A61C 8/006* (2013.01); *A61C 8/0072* (2013.01); *A61C 13/083* (2013.01)

(58) Field of Classification Search
CPC ......... A61C 8/005–8/0075; A61C 5/70; A61C 5/30; A61C 5/35; A61C 5/73
See application file for complete search history.

(56) References Cited

U.S. PATENT DOCUMENTS

| | | | | |
|---|---|---|---|---|
| 4,850,873 A | * | 7/1989 | Lazzara | A61C 8/0048 433/173 |
| 5,759,034 A | | 6/1998 | Daftary | |
| 6,048,203 A | * | 4/2000 | Rosenberg | A61C 8/0048 433/172 |
| 6,648,645 B1 | * | 11/2003 | MacDougald | A61C 5/002 433/212.1 |
| 6,824,386 B2 | * | 11/2004 | Halldin | A61C 8/0001 433/173 |
| 6,939,135 B2 | * | 9/2005 | Sapian | A61C 8/005 433/174 |
| 8,092,219 B2 | | 1/2012 | Neumeyer | |
| 8,371,851 B2 | | 2/2013 | Smith et al. | |

(Continued)

FOREIGN PATENT DOCUMENTS

CA    2611942    12/2006

OTHER PUBLICATIONS

International Searching Authority, International Search Report and Written Opinion relating to application No. PCT/CA2015/050467.

*Primary Examiner* — Edward Moran
(74) *Attorney, Agent, or Firm* — Rowand LLP (57) ABSTRACT

A dental abutment, or a dental implant having an integrated abutment, in which the occlusal part of the abutment to which the dental prosthesis is to be cemented features a shoulder having a reverse margin. At the point where the shoulder meets the outer profile of the gingival part of the abutment, the shoulder is at an acute angle with respect to the longitudinal center axis of the abutment, thereby causing any cement ejected during mounting of the prosthesis to be ejected in a direction away from the gingiva.

13 Claims, 6 Drawing Sheets

(56) References Cited

U.S. PATENT DOCUMENTS

| | | |
|---|---|---|
| 2006/0122719 A1* | 6/2006 | Kopelman ......... A61C 13/0004 700/98 |
| 2007/0037122 A1* | 2/2007 | Bassett ................ A61C 8/0001 433/173 |
| 2008/0014556 A1* | 1/2008 | Neumeyer ........... A61C 8/0022 433/174 |
| 2008/0057476 A1 | 3/2008 | Zettler et al. |
| 2008/0274440 A1* | 11/2008 | Smith .................... A61C 8/005 433/174 |
| 2011/0129797 A1* | 6/2011 | Neumeyer ........... A61C 8/0001 433/173 |
| 2012/0077150 A1 | 3/2012 | Goodman et al. |
| 2012/0164602 A1 | 6/2012 | Lussi et al. |
| 2012/0308960 A1 | 12/2012 | Mashio et al. |
| 2014/0147812 A1 | 5/2014 | Ilter et al. |
| 2015/0017604 A1 | 1/2015 | Kern |

* cited by examiner

DENTAL PROSTHESES CEMENTED ONTO IMPLANTS AND/OR ABUTMENTS HAVING A REVERSE MARGIN

FIELD

The present application generally relates to dental prostheses and, in particular, to dental implants or abutments to which dental prostheses are cemented.

BACKGROUND

Crowns and other dental prostheses are often attached to teeth or implants in the mouth by way of dental cement, i.e. a dental luting agent. A dental implant system for retaining a dental prosthesis typically has a threaded shaft for connection to the bone and an occlusal projection onto which the dental prostheses is to be cemented. This occlusal projection may be termed an abutment. In some cases, the occlusal part of the implant (the abutment) and the sub-gingival portion of dental implant that attaches to the jaw (upper or lower) are a unified piece. In some other cases, the dental implant system has two-parts: a dental implant to be secured to the jaw and an abutment to be later secured to the dental implant.

The prosthesis is cemented with a luting agent/dental cement to the abutment, whether it is an intermediary piece of a two-part implant system or whether it is part of a unified dental implant. The typical dental abutment or integrated implant system has an occlusal portion with a sloped shoulder. The dental prosthesis is seated on the occlusal portion and abuts the sloped shoulder in close alignment. During attachment, cement between the dental prosthesis and the occlusal portion is compressed and extruded through the interface between the prosthesis and the sloped shoulder. The extrusion may cause cement to be injected below the gingiva, which may lead to irritation and inflammation and even loss of the dental implant.

It would be advantageous to provide for dental implants, abutments and prostheses that reduce the injection of luting agent/cement below the gingiva.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

In a first aspect, the present application describes a dental abutment for attachment to a dental implant for supporting attachment of a dental prosthesis by cementation with a luting agent to the dental abutment. The dental abutment includes a main body having a gingival part for attachment to the dental implant and an occlusal part to support cementation of the dental prosthesis onto the dental abutment with the luting agent, the main body having a longitudinal center axis. The occlusal part of the main body has an outer profile radially closer to the longitudinal center axis than an outer profile of the gingival part at the interface between the occlusal part and the gingival part, thereby defining a shoulder between the occlusal part and the gingival part. The outer profile of the gingival part at a point where it meets the shoulder is generally parallel to the longitudinal center axis, and a face of the shoulder that meets the outer profile of the gingival part at the point is at an acute angle with respect to the longitudinal center axis.

The present application further discloses a dental restoration system that includes the dental abutment and a dental prosthesis to be cemented to the dental abutment. The dental prosthesis includes an occlusal body having defined therein a cavity with an inner wall, the inner wall having a profile corresponding to the outer profile of the occlusal part of the dental abutment and a margin generally parallel to and facing the shoulder of the dental abutment, when mounted to the dental abutment.

In yet another aspect, the present application describes dental prosthesis to be cemented to a dental abutment. The dental prosthesis includes a main body having an outer occlusal surface and having defined therein a cavity with an inner wall, the inner wall having a profile corresponding to an outer profile of an occlusal part of the dental abutment and a margin connecting the inner wall to the outer occlusal surface, the cavity having a longitudinal center axis generally to be aligned with a center axis of the dental abutment. The outer occlusal surface at a point where it meets the margin is generally parallel to the longitudinal center axis, and a face of the margin that meets the outer occlusal surface at the point is at an obtuse angle with respect to the longitudinal center axis.

In yet a further aspect, the present application describes a dental implant system for supporting attachment of a dental prosthesis by cementation to the dental implant system. The dental implant system including a main body having a gingival part and an occlusal part to support cementation of the dental prosthesis onto the dental implant system, the main body having a longitudinal center axis, and a threaded shaft depending from the gingival part of the main body to attach the dental implant system to bone. The occlusal part of the main body has an outer profile radially closer to the longitudinal center axis than an outer profile of the gingival part at the interface between the occlusal part and the gingival part, thereby defining a shoulder between the occlusal part and the gingival part. The outer profile of the gingival part at a point where it meets the shoulder is generally parallel to the longitudinal center axis, and a face of the shoulder that meets the outer profile of the gingival part at the point is at an acute angle with respect to the longitudinal center axis.

Other aspects and features of the present application will be understood by those of ordinary skill in the art from a review of the following description of examples in conjunction with the accompanying figures.

In the description that follows, references will be made to dental restorations, i.e. prostheses, which will be understood to include crowns, retainers or other dental prosthetics typically cemented to a dental abutment or dental implant using a cement/luting agent. It will be appreciated that a dental abutment is generally a body onto which prosthesis mounted. The abutment is often a separate physical element from the dental implant since the implant is secured to a jawbone and the separate abutment allows for fine tuning of location/depth and, sometimes, angle of abutment such that the dental prosthesis ends up with correct location, orientation and support. The abutment may also be part of an integrated one-piece dental implant system. In such a case, references herein to the abutment will be understood as alternatively being applied to a separate abutment or to a dental implant system that incorporates and integrated abutment portion. References to a dental prosthetic or a dental restoration will be understood to be interchangeable terms and to include crowns, retainers, or other prosthetics intended to be attached to a dental implant system by way of a dental luting agent or dental cement.

The terms "cement", "dental cement", and "luting agent" are used interchangeably in the present application. In all instances, they are intended to refer to luting agents used to bind or cement two components together within the mouth and, in particular, to cementation compounds used to bind a dental prosthetic to an abutment.

The example implants, abutments and/or restorations depicted and discussed herein are shown in the figures, for consistency and ease of understanding, in the orientation used when mounting to the mandible (lower jaw); that is, with the biting/occlusal surface "up" and the attachment structure to be secured to the jaw or supporting tissues "down". It will be appreciated that implants and restorations may be used in the maxilla (upper jaw), in which case the biting/occlusal surface might be considered "down". To avoid confusion, the terms "up" or "upper" and "down" or "lower" are avoided in the present application since their meaning may depend on whether the applicable element is used in the maxilla or the mandible. The term "occlusal" refers to the biting surface and "gingival" refers to the attachment structure intended to be secured to the bone and/or gingiva or other supporting tissues.

Figure 1:
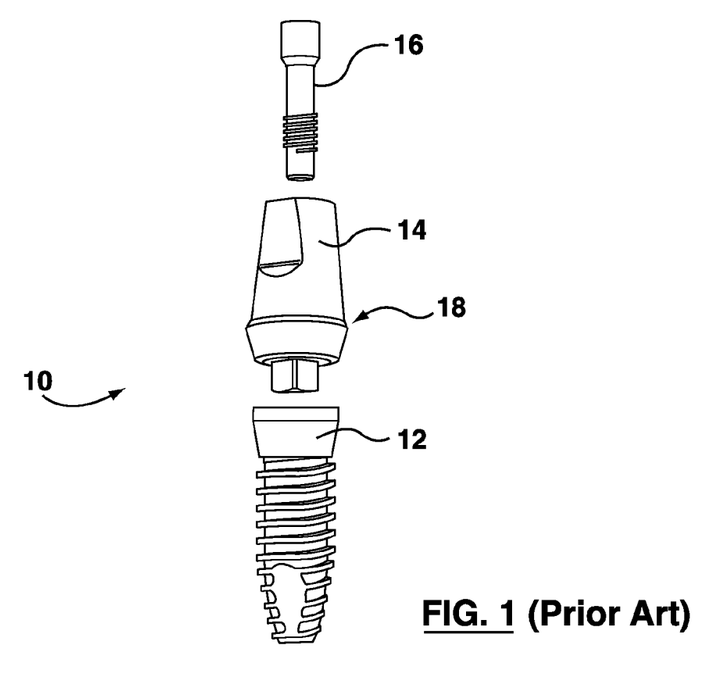
FIG. 1 shows a side view of an example of a dental implant and a dental abutment.

Reference is first made to FIG. 1, which shows a perspective view of an example dental implant system 10. The dental implant system 10 is for tooth root replacement and to support a dental prosthesis (not shown). A typical dental implant system 10 includes a dental implant 12 and an abutment 14. This example dental implant 12 features a threaded shaft and a central bore. The abutment 14, in this example includes an axial passageway through which a screw 16 is inserted to secure the abutment 14 to the central bore of the dental implant 12. Mounted intraorally, the abutment 14 projects outwards from the gingiva and provides a (typically generally frustoconical) post onto which a prosthesis (not shown) may be mounted. The prosthesis is attached to the abutment intraorally using a luting agent, such as dental cement. In other examples, the abutment 14 may not feature an axial passageway and may, instead, have an axial threaded shaft so that the abutment 14 is screwed into place on the dental implant 12. In yet other examples, the abutment 14 may be friction fit to the dental implant 12 or attached in some other way.

In the example shown in FIG. 1, the abutment 14 includes a shoulder 18 below the generally frustoconical post portion. The shoulder 18 serves to support and abut the cemented end of the prosthesis to give support to the prosthesis. The shoulder 18 may be referred to as the "margin" of the abutment 14. The terms shoulder and margin may be used interchangeably herein.

Figure 2:
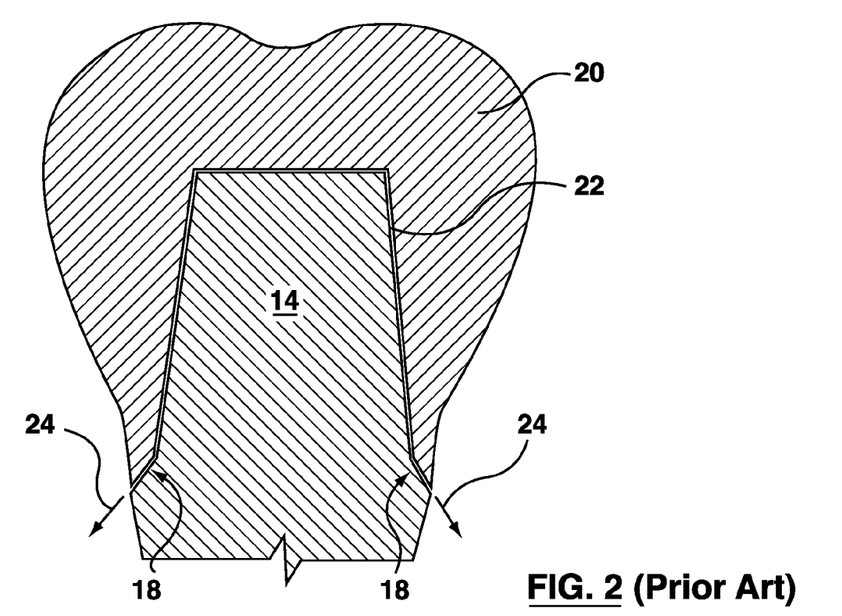
FIG. 2 shows a cross-sectional view of an example crown cemented to an example dental abutment.

Reference is now made to FIG. 2, which shows a cross-sectional view of a portion of the abutment 14 and a prosthesis, which in this example is a crown 20. The crown 20 is attached to the abutment 14 using a dental cement 22. The crown 20 has an interior profile generally shaped to correspond to the exterior profile of the end of the abutment 14 to which it is to be cemented. The dental cement 22 retains the crown 20 on the abutment 14 and, usually, eliminates any gaps or spaces between the crown 20 and abutment 14 that would otherwise harbour microbes and cause inflammation of surrounding tissues.

The exterior surface of the crown 20 is often shaped to have a profile that results in a smooth transition between the surface of the crown 20 and the outer surface of the gingival part of the abutment 14 where the shoulder 18 meets the outer surface, so as to avoid any discontinuities or visible transition lines. The abutment 14 is often formed from a metal, such as titanium, zirconium, titanium alloy, or combinations thereof. For aesthetic reasons, the abutment 14 and crown 20 are often designed, particularly with modern custom abutments, such that the shoulder 18 is at or below the gingiva, at least for those crowns that would be visible to others once in place.

The shoulder 18 shown in FIGS. 1 and 2 slopes outwards and towards the gingiva (i.e. away from the apex (occlusal surface) of the crown 20). When mounting the crown 20, the cement 22 is compressed and may be expelled from the interface between the crown 20 and the shoulder 18. With the shoulder 18 sloped towards the gingiva, it tends to eject cement into the gingiva, as indicated by arrows 24. Ideally, to reduce subsequent leakage and visible discontinuities or gaps that may allow microbes to grow, the outer edge of the crown 20 profile meets the outer edge of the shoulder 18. Due to manufacturing inaccuracies, such a fit is often imperfect, but if the shoulder 18 and the corresponding facing inner profile of the crown 20 taper to a pinch-point at the outer edge, then the hydraulic pressure built up through compressing the cement while seating the crown 20 in place on the abutment 14 causes the cement to be expelled from the shoulder-crown interface at high velocity, projecting it downwards into or under the gingiva.

Cement injected under the gingiva leads to irritation to the gingiva and the tissues of the jaw in general. In some cases, cement leads to inflammation of the gingiva and bone supporting the dental implant, and can lead to failure of the hard connection between the dental implant and surrounding tissues.

Even with post-attachment cleaning, it is extremely difficult to remove cement extruded from the interface between the crown 20 and the abutment 14, partly due to the difficulty in visibly observing and accessing the area after installation of the crown 20. Notably, the gingival attachment around a dental implant is different from that of a natural tooth. A healthy natural tooth has collagen fibers that hold the gums against the root surface, however these fibers do not exist around dental implants. Accordingly, the gums fit more loosely around dental implants, leaving a greater possibility for cement to be injected under the gingiva.

In accordance with one aspect of the present application, dental abutments and corresponding prostheses incorporate a "reverse margin", i.e. a shoulder that, at the edge where it meets the outer surface of the gingival end of the abutment, is angled away from the gingiva. In other words, the face of the shoulder at the point where it meets the outer profile of the abutment is at an acute angle to the longitudinal axis of the abutment. Accordingly, the reverse margin tends to direct extruded/projected luting agent out of or away from the gingiva, rather than into it.

Figure 3A:
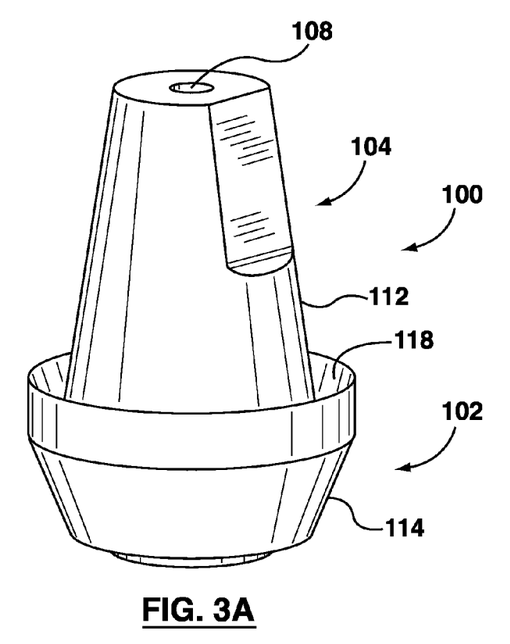
FIG. 3A shows a perspective view of one example of a dental abutment with a reverse margin.
Figure 3B:
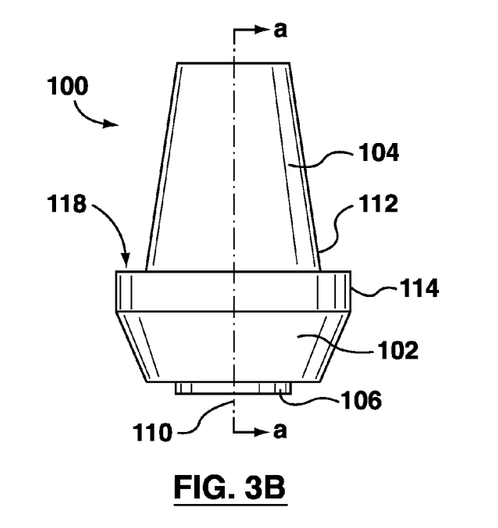
FIG. 3B shows a side view of the example dental abutment of FIG. 3A.
Figure 3C:
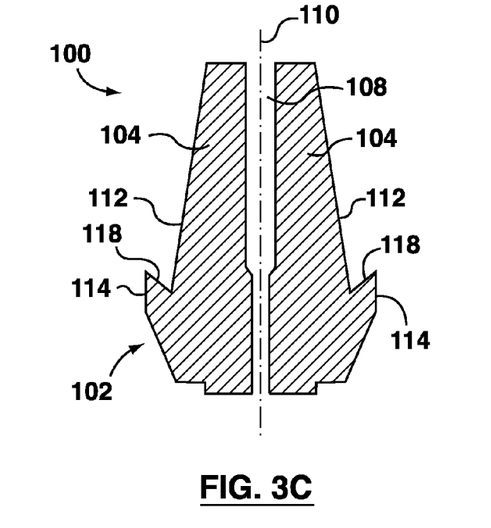
FIG. 3C shows a cross-sectional view of the example dental abutment of FIG. 3B along the line a-a.

Reference is now made to FIGS. 3A, 3B and 3C, which show one example of an abutment 100 having a reverse margin. FIG. 3A shows a perspective view, FIG. 3B shows a side view, and FIG. 3C shows a cross-section view along a longitudinal plane a-a.

The example abutment 100 is a generally cylindrical main body that includes a gingival part 102 to be attached to a dental implant and an occlusal part 104 to which a prosthesis is to be cemented. In some embodiments, the distal end of the gingival part 102 may include a narrowed portion 106 that provides a rotational lock profile, such as a square, hex, or keyed profile that fits a corresponding cavity in the dental implant to secure the abutment 100 against rotation. The abutment 100 in this example includes a bore or central passageway 108. In this example, the central passageway 108 is coaxial with a longitudinal center axis 110 of the abutment 100. A screw (not shown) or other attachment mechanism may be inserted into the central passageway 108 to secure the abutment 100 to a dental implant. It will be appreciated that in other example embodiments, the abutment 100 may have no central passageway 108 and may have a threaded shaft or other attachment mechanism for securing the abutment 100 to a dental implant.

The occlusal part 104 of the abutment 100 includes an outer surface or profile 112. The gingival part 102 includes an outer surface or profile 114 that is a further radial distance from the longitudinal center axis 110 than the outer profile 112 at the interface between the gingival part 102 and the occlusal part 104. The outer profiles 112 and 114 are joined by a shoulder 118. The shoulder 118, at the point where the shoulder 118 meets the outer profile 114 of the gingival part 102, is at an acute angle with respect to the longitudinal axis. In other words, a vector normal to the face of the shoulder 118 at that point projects through the longitudinal axis. This sloping of the shoulder 118 such that it is angled away from the gingiva assists in ensuring that cement that is projected from between the crown-abutment interface, i.e. the margin/shoulder, is projected away and out from the gingiva rather than towards and into the gingiva. The acute angle between the face shoulder at the point where it meets the outer profile 114 of the gingival part 102 may be between 89 and 30 degrees in some examples.

The outer profile 114 of the gingival part 102 is generally parallel to the longitudinal axis at the point where it meets the shoulder 118. In some examples, the outer profile 114 at that point may be tapered slightly towards the distal end of the gingival part. In some examples, the tapering may be between 0 and 20 degrees.

Figure 4:
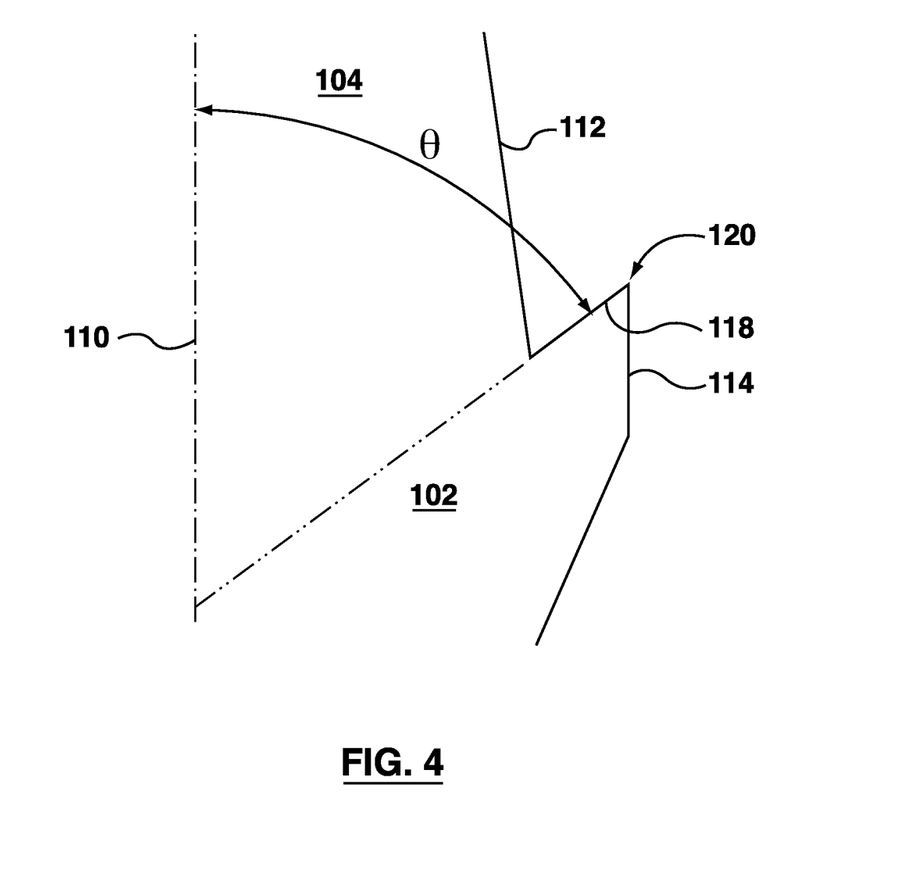
FIG. 4 shows a close-up cross-sectional view of the shoulder of the example dental abutment of FIG. 3C.

FIG. 4 shows a partial cross-sectional view of the shoulder portion of the abutment 100. In this example, the shoulder 118 is planar in cross-section. The face of the shoulder 118 is thus at a consistent acute angle θ with respect to the longitudinal center axis 110. Reference numeral 120 indicates the point where the shoulder 118 meets the outer profile 114 of the gingival part 102. The portion of the shoulder 118 proximate the point 120 is angled so as to extend outwards in an occlusal direction as opposed to a gingival direction.

It will be appreciated that the entire shoulder face between the outer profile 112 and the outer profile 114 is not necessarily at an acute angle with respect to the longitudinal center axis 110, but the face of the portion of shoulder 118 proximate the point 120 is at an acute angle with respect to the longitudinal center axis 110.

In some examples, as shown in FIG. 4, the shoulder 118 is planar in cross-section, and it meets the outer profile 112 of the occlusal part 104 at a sharp acute angle. In some examples, the shoulder 118 is generally planar in cross-section at the point 120 where it meets the outer profile 114 of the gingival part 102, but the interface between the shoulder 118 and the outer profile 112 of the occlusal part 104 is a concave curve (not shown). The latter arrangement may result in cases where the margin is carved or machined into the main body using a cutting tool.

The outer profiles 112 and 114 are generally cylindrical and generally parallel to the longitudinal center axis 110. In many examples, the outer profile 112 of the occlusal part 104 is sloped, curved or tapered inwards towards its apex to facilitate seating of the dental prosthesis on the occlusal part 104. The outer profile 114 of the gingival part 104 is generally parallel to the longitudinal center axis 110 at the point 120 where it meets the shoulder 118. In some examples, the outer profile 114 of the gingival part 104 may taper or curve inwards towards the gingival end of the gingival part 104 where it is to meet and mount to the dental implant. Either or both of the outer profiles 112 and 114 may be keyed in part to prevent rotation relative to the prosthesis or dental implant, respectively, once mounted.

Figure 5:
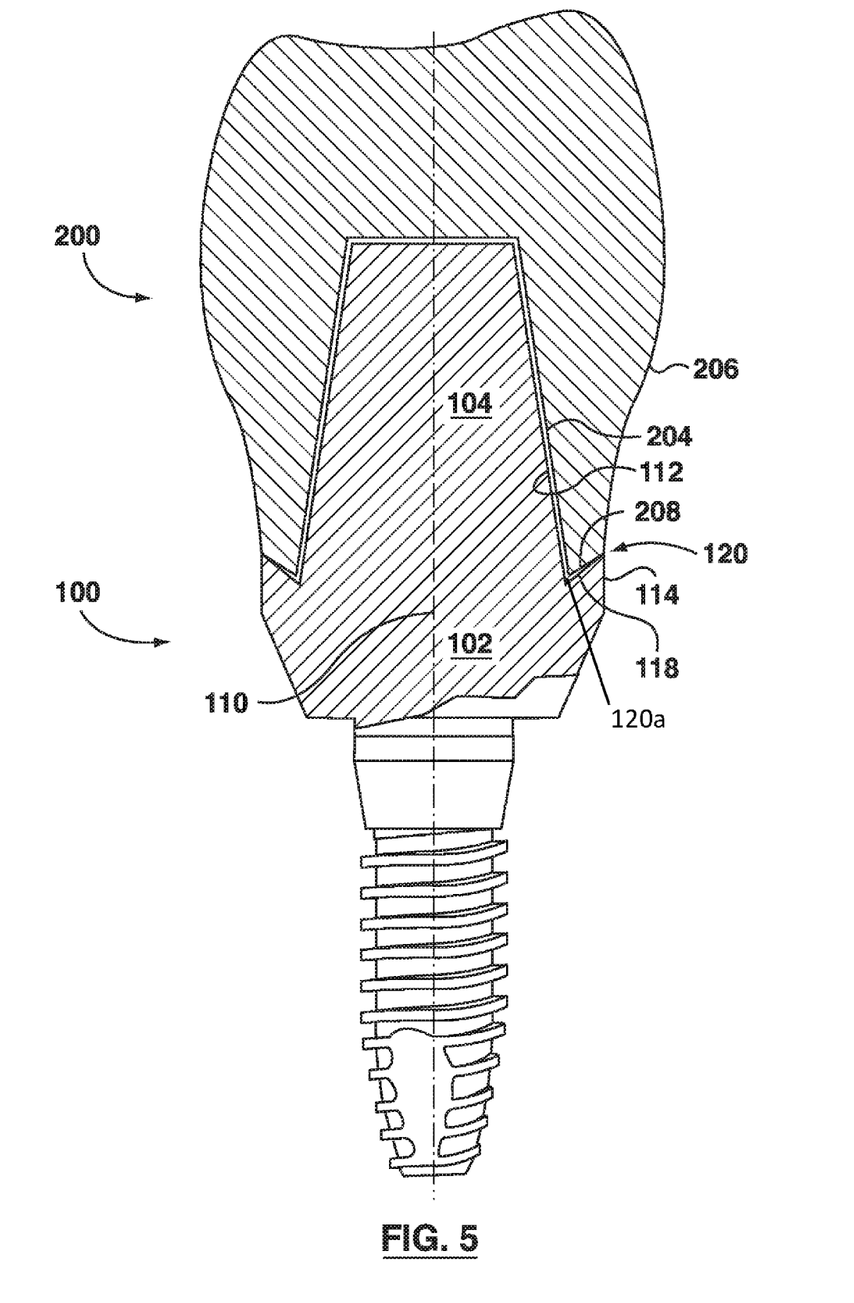
FIG. 5 shows a cross-sectional view of an example crown cemented to the example dental abutment.

Reference is now made to FIG. 5, which shows a partial cross-sectional view of the abutment 100 and a crown 200. The crown 200 in this example is a solid mass formed to have an occlusal end 202 and an internal cavity defined by an inner wall 204. The internal cavity is sized to fit with the occlusal part 104 of the abutment 100. The inner wall 204 may be shaped to generally correspond in shape to the outer profile 112 of the occlusal part 104. The crown is completely solid along and between the entire outer surface and inner wall.

In some cases, the crown 200 is formed from ceramic. Using CAD/CAM technology, the crown 200 may be created as a 3-dimensional model and a solid ingot of ceramic may then be milled to create the modeled crown. In some other instances, crowns are made from metal (e.g. gold) or from porcelain-fused-to-metal.

The example crown 200 has an outer surface 206, which is generally parallel to the longitudinal center axis 110 at the point 120 where it meets the outer edge of the shoulder 118. The outer surface 206 and outer profile 114 are ideally created to be generally contiguous at the point 120 so as to lessen any gaps and any visible discontinuities.

The inner wall 204 includes margin 208. The margin 208 corresponds to and faces the shoulder 118. In this example, the margin 208 is generally parallel with the shoulder 118, although it tapers slightly relative to the face of the shoulder 118 so as to contact the shoulder 118 at its outer edge, i.e. at point 120. The taper relative to the shoulder 118 may be approximately 1 to 5 degrees in some embodiments. Just as the face of the shoulder 118 at the point 120 forms an acute angle with the longitudinal center axis 110, so the face of the margin 208 at the point 120 forms an obtuse angle with the longitudinal center axis 110.

To mount the crown 200 to the abutment 100, the cement is place on the inner wall 204 of the cavity and the crown 200 is pressed into place on the occlusal part 104 of the abutment 100. The pressure on the crown 200 compresses and extrudes the cement throughout the interface between the inner wall 204 and the outer profile 112, including between the margin 208 and the shoulder 118. Excess cement may be ejected through the point 120 where the outer edge of the margin 208 meets the outer edge of the shoulder 118 while a space 120A is maintained between the margin and the shoulder closer to the longitudinal axis in which the dental cement fills in. The angles of the margin and shoulder 118 relative to the longitudinal center axis 110 in this example ensure the cement ejected is ejected away from and out of the gingiva rather than towards and under the gingiva.

Figure 6:
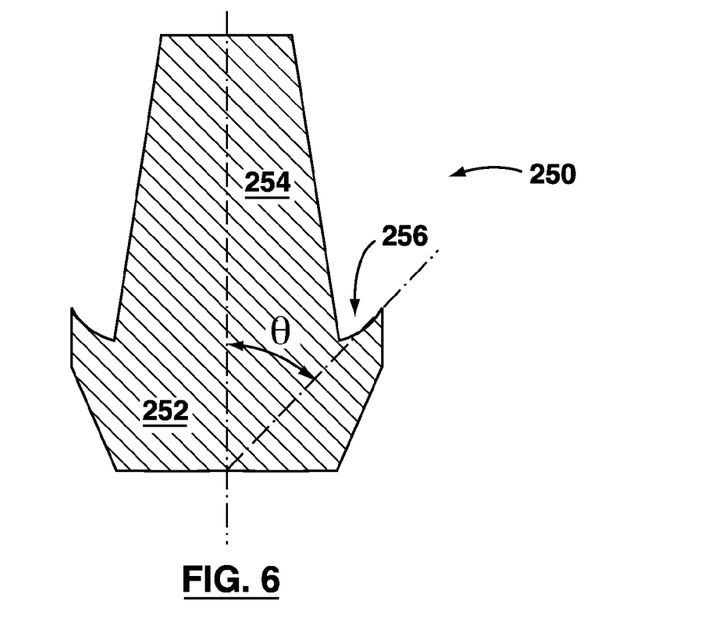
FIG. 6 shows a cross-sectional view of another example abutment.

Reference is now made to FIG. 6, which shows another simplified example cross-section of an abutment 250. The abutment 250 includes a gingival part 252 to be attached to a dental implant (not shown) and an occlusal part 254 to which a dental prosthesis is to be cemented. A shoulder 258 is formed at the interface between the occlusal part 254 and the gingival part 252. At least a portion of the face of the shoulder 258 in this example is concave in cross-section. The face of the shoulder 258 at its outer edge where it meets the outer profile of the gingival part 252 forms an acute angle θ with a longitudinal center axis 256 of the abutment.

Figure 7:
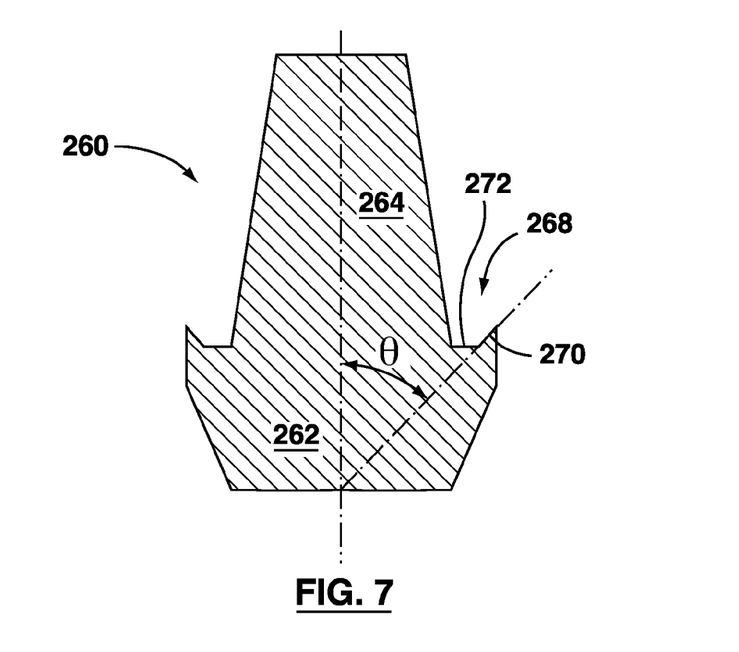
FIG. 7 shows a cross-sectional view of yet another example abutment.

Reference is now made to FIG. 7, which shows yet another simplified example cross-section of an abutment 260. The abutment 260 includes a gingival part 262 and an occlusal part 264. A shoulder 268 between the gingival part 262 and the occlusal part 264 includes a face portion 270 that defines the outer edge of the shoulder 268 where it meets the outer profile of the gingival part 262. The face portion 270 forms an acute angle with the longitudinal center axis of the abutment 260. The shoulder 268 further includes one or more other faces or portions connecting the face portion 270 to the outer profile of the occlusal portion 264. In this illustrated example, the shoulder 268 includes a substantially planar radial face 272.

The margin or shoulder in other examples may have yet other shapes. Moreover, it will be understood that the shoulder is not necessarily annular, i.e. it may vary in its distance from the occlusal end of the abutment. In some cases, the shoulder is customized to correspond to the expected level of the gingiva when the abutment is in place within the mouth. Accordingly, it may vary in width and in distance from the occlusal end so that the outer edge of the shoulder has a contour that corresponds to the gingiva, particularly for those portions of the abutment that would otherwise be visible in the smile.

Figure 8:
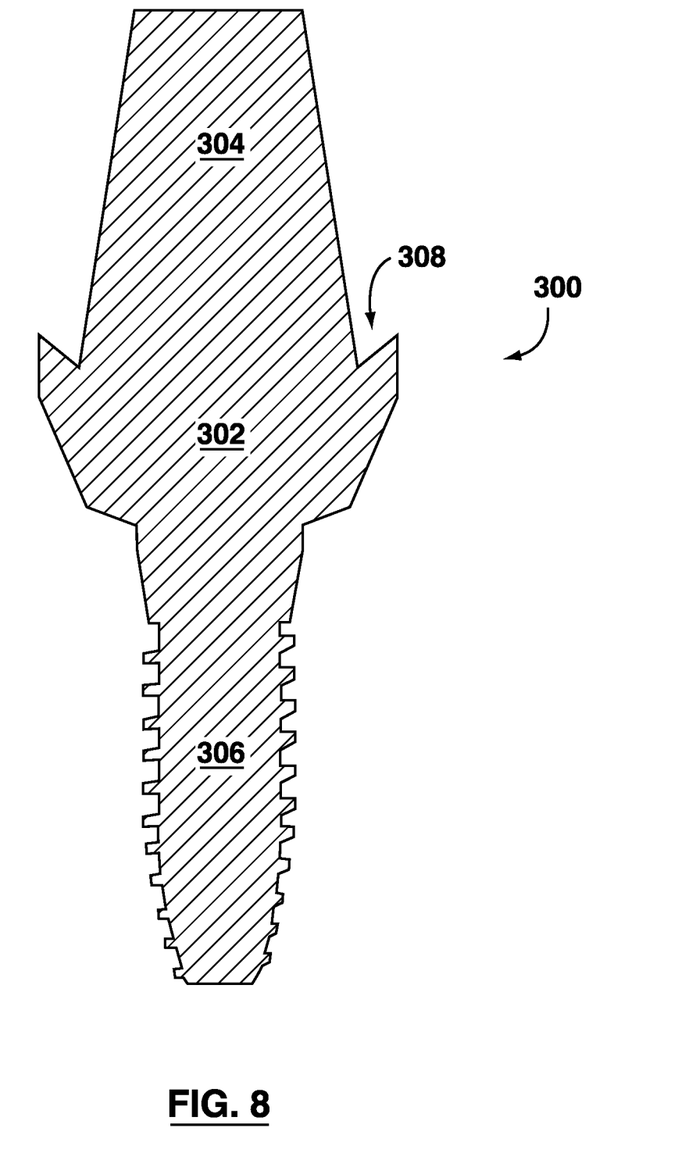
FIG. 8 shows a cross-sectional view of an example dental implant system with an integrated abutment, and without showing a cemented dental restoration.

Reference is now made to FIG. 8, which shows an example unitary dental implant system 300. The dental implant system 300 is one in which the dental implant and abutment are formed as a single piece. With the dental implant system 300, there is no separate abutment piece to be mounted to the dental implant; rather, the implant itself features the protruding occlusal post onto which a prosthesis is to be cemented using a luting agent. The dental implant system 300 in this example is formed from a main body of generally cylindrical shape. The main body includes an occlusal part 304 to which a dental prosthesis, such as a crown, is to be cemented. The main body also includes a gingival part 302, from which a threaded shaft 306 extends in this example. The threaded shaft 306 is for attachment to a jawbone or other supporting structure.

The dental implant system 300 features a reverse margin shoulder 308 formed at the interface between the occlusal part 304 and the gingival part 302. As described in earlier embodiments, the shoulder 308 includes a face which meets the outer profile of the gingival part 302 and which forms an acute angle with a longitudinal central axis of the dental implant system 300.

Certain adaptations and modifications of the described embodiments can be made. Therefore, the above discussed embodiments are considered to be illustrative and not restrictive.

What is claimed is:

1. A dental restoration system, comprising:
   a dental abutment formed from a main body having a gingival part for attachment to a dental implant and an occlusal part, the main body having a longitudinal center axis,
      wherein the occlusal part of the main body has an outer profile radially closer to the longitudinal center axis than an outer profile of the gingival part at an interface between the occlusal part and the gingival part, thereby defining a shoulder between the occlusal part and the gingival part,
      and wherein a face of the shoulder that meets the outer profile of the gingival part at a maximum radial distance of the outer profile from the longitudinal axis is at an acute angle opening toward the occlusal part with respect to the longitudinal center axis; and
   a dental prosthesis cemented to the dental abutment using dental cement, the dental prosthesis comprising an occlusal body with an outer surface and having defined therein a cavity with an inner wall, the prosthesis being completely solid along and between the entire outer surface and inner wall, the inner wall having a profile corresponding to the outer profile of the occlusal part of the dental abutment and a margin facing the shoulder of the dental abutment, when mounted to the dental abutment, and wherein the margin is generally parallel to the shoulder but tapered with respect thereto, so as to make contact with the face of the shoulder proximate its maximum radial distance while maintaining a space between the margin and shoulder closer to the longitudinal axis in which the dental cement fills in,
   wherein the acute angle is within the range 30 to 89 degrees,
   and whereby during mounting of the dental prosthesis to the dental abutment an excess portion of the dental cement is extruded between the margin and the shoulder in a direction away from gingiva.

2. The dental restoration system claimed in claim 1, wherein the margin is tapered at an angle of less than 5 degrees and more than 1 degree relative to the shoulder.

3. The dental restoration system of claim 1, wherein at least a portion of the shoulder is curved in longitudinal cross-section.

4. The dental restoration system of claim 3, wherein the curved portion of the shoulder is concave.

5. The dental restoration system of claim 1, wherein the outer profile of the gingival part at a point where it meets the shoulder is parallel to the longitudinal center axis.

6. The dental restoration system of claim 1, wherein the outer profile of the occlusal part tapers inwards towards an apical end of the occlusal part, and wherein the outer profile of the gingival part tapers inwards towards a distal end of the gingival part.

7. The dental restoration system of claim 1, wherein the outer profile of the occlusal part and the face of the shoulder comprises cementation surfaces to which the dental prosthesis is affixed using the cement.

8. The dental restoration system of claim 1, wherein the main body defines an axial passageway therethrough for receiving an axial screw to secure the dental abutment to the dental implant.

9. The dental restoration system of claim 1, wherein the gingival part includes a threaded shaft for securing the dental abutment to the dental implant.

10. The dental restoration system of claim 1, wherein the main body comprises a single piece of material.

11. The dental restoration system claimed in claim 1, further comprising the dental implant adapted to be connected to bone and upon which the dental abutment is to be mounted.

12. The dental restoration system claimed in claim 1, further comprising the dental implant adapted to be connected to bone and formed together with the dental abutment as an integrated piece.

13. The dental restoration system claimed in claim 1, wherein the dental prosthesis is wholly formed from ceramic or porcelain.

* * * * *